United States Patent
Takahashi

US006352727B1

(10) Patent No.: US 6,352,727 B1
(45) Date of Patent: Mar. 5, 2002

(54) BACTERICIDES

(75) Inventor: Tetsunari Takahashi, Tokyo (JP)

(73) Assignees: Oji Paper Co., Ltd.; Eishogen Co., Ltd., both of Tokyo (JP)

(*) Notice: Subject to any disclaimer, the term of this patent is extended or adjusted under 35 U.S.C. 154(b) by 0 days.

(21) Appl. No.: 09/623,453

(22) PCT Filed: Mar. 11, 1999

(86) PCT No.: PCT/JP99/01183

§ 371 Date: Sep. 11, 2000

§ 102(e) Date: Sep. 11, 2000

(87) PCT Pub. No.: WO99/45784

PCT Pub. Date: Sep. 16, 1999

(30) Foreign Application Priority Data

| Mar. 12, 1998 | (JP) | 10-061799 |
| Mar. 12, 1998 | (JP) | 10-061800 |
| Mar. 31, 1998 | (JP) | 10-087782 |
| Apr. 1, 1998 | (JP) | 10-089052 |

(51) Int. Cl.[7] .................. A61K 35/28; A61K 31/72; A01N 65/00; A61L 2/00

(52) U.S. Cl. .................. 424/742; 47/57.6; 424/404; 424/439; 424/442; 424/443; 424/78.07; 426/270; 426/298; 426/309; 426/310; 426/332; 426/335; 504/100; 504/101; 514/55; 514/859; 514/865

(58) Field of Search ............... 424/742, 404, 424/439, 442, 443, 78.07; 514/55, 865, 859; 47/57.6; 426/270, 298, 309, 310, 332, 335; 504/100, 101

(56) References Cited

U.S. PATENT DOCUMENTS 5,536,155 A * 7/1996 Futaki et al. ............. 514/25

FOREIGN PATENT DOCUMENTS

| JP | 52102421 | 8/1977 |
| JP | 58-39615 | 3/1983 |
| JP | 59-46208 | 3/1984 |
| JP | 59-46223 | 3/1984 |
| JP | 62289511 | 12/1987 |
| JP | 2-35065 | 2/1990 |
| JP | 4-316506 | 11/1992 |
| JP | 5-306252 | 11/1993 |
| JP | 6-340484 | 12/1994 |
| JP | 7-33602 | 2/1995 |

OTHER PUBLICATIONS

English Language Abstract of JP 2–35065; 2–90.
English Language Abstract of JP 4–316506; 11–92.
English Language Abstract of JP 5–306252; 11/93.
English Language Abstract of JP 58–39615; 3/83.
English Language Abstract of JP 59–46208; 3/84.
English Language Abstract of JP 59–46223; 3/84.
English Language Abstract of JP 6–340484; 12/94.
English Language Abstract of JP 7–33602; 2/95.
English Language Abstract of JP 52–102421.; 8/77.
English Language Abstract of JP 62–289511; 12/87.
Nakayama, R. et al., Antibacterial Compounds from *Eucalyptus perriniana*, Agric. Biol. Chem., 54, 231–232 (1990).
Murata, M. et al., Macrocarpal A, a Novel Antibacterial Compound from *Eucalyptus macrocarpa*, Agric. Biol. Chem., 54(1), 231–232 (1990).
Kendra, D. and Hadwiger, L., Characterization of the Smallest Chitosan Oligomer that is Maximally Antifungal to *Fusarium solani* and Elicits Pisatin Formulation in *Pisum Sativum*, Experimental Mycology 8, 276–281 (1984).
Uchida, Y., Antibacterial activity of chittin and chitosan, Food Chemical 2, 22 (1988).
Lamberton, J., The Occurence of 5–Hydroxy–7, 4'–Dimethoxy–6–Methyflavone in Eucalyptus Waxes, Aust. J. Chem., 17, 692–696 (1964).
Horn, D. et al., The Composition of Eucalyptus and some other Leaf Waxes, Aust. J. Chem., 17, 464–476 (1964).
Saeki, T. et al., Antibacterial Activity of Peppermint Essential Oil and its Component against Enteric Canal *Hemorraghic Coli* 0157 and Effect Combined with Green Tea Polyphenol, The 25th Annual Symposium Paper of Nippon Antibacterial and Antifungal Society, May 26–27, 1998.
Nishimura, H., Mirai no Seibutsu Shigen Yukari, 1987, with Partial English Translation.

* cited by examiner

Primary Examiner—Herbert J. Lilling
(74) Attorney, Agent, or Firm—Greenblum & Bernstein, P.L.C.

(57) ABSTRACT

An object of the present invention is to provide a bactericide (and a fungicide) that is highly safe and has strong bactericidal power even when used in low concentration, and that can be used repeatedly in a sterilizing process.

The object can be achieved by the bactericide (or the fungicide) comprising a polar solvent extract of leaves of eucalyptus plants and chitosan. The polar solvent is preferably chosen from the group consisting of lower alcohols and glycols.

29 Claims, No Drawings

BACTERICIDES

TECHNICAL FIELD

The present invention relates to a bactericide (and a fungicide) originated from natural products. More specifically, the present invention relates to a bactericide (and a fungicide) containing an extract obtained by extraction from leaves of eucalyptus plants into a polar organic solvent and chitosan, or a bactericide (and a fungicide) containing glycerol fatty acid ester in addition to the above-mentioned components, which has strong and persistent bactericidal (or fungicidal) power and high safety.

The bactericide (and a fungicide) of the present invention can be used at home, restaurants, medical facilities, old-age homes, abattoir facilities, cattle sheds, chicken houses, and the like. Particularly, the present invention is useful as a bactericide (and a fungicide) for preventing an acne, athlete's foot.

BACKGROUND TECHNOLOGY

There are about six hundred species of eucalyptus plants, of which an essential oil or an ethanol extract or the like are used as pharmaceuticals, quasi-drugs, food additives and perfumery, such as pharmaceuticals for asthma, preservatives, aromatic substances (Hiroyuki Nishimura, "Mirai no Seibutsu Shigen Yukari", 1987). It has been reported that cineole that is a major component of eucalyptus essential oil has an effect as antiseptics, or enhances an effect of antibacterial substance (bisbiguanide compound) (Japanese Patent Application Laid-open publication (KOKAI) publication No. Sho 62-289511). It has been reported that grandinol isolated from an organic solvent extract of *Eucalyptus perriniana* (Agric. Biol. Chem., 54, 1, 231, 1990) and Macrocarpal-A isolated from *Eucalyptus macrocarpa* (Agric. Biol. Chem., 54, 12, 3221) have antibacterial activity against *Staphylococcus aureus* and *Bacillus subtilis*.

Chitosan is a compound produced by deacetylating chitin contained in a carapace of a crab or the like, and is also used as a food additive. It has been reported that chitosan has an antibacterial activity against Fusarium, *Escherichia coli, Staphylococcus aureus, Bacillus subtilis* or the like (Experimental Mycology 8, 276, 1984, Food chemical 2, 22, 1988).

There have been reported examples of a synergy effect achieved by mixing two or more of antibacterial components, such as rifampicin and chitosan (Japanese Patent Application Laid-open publication (KOKAI) No.59-46208), sulfonamides and chitosan (Japanese Patent Application Laid-open publication (KOKAI) No.59-46223), chitosan and ascorbic acid (Japanese Patent Application Laid-open publication (KOKAI) No. 2-35065), organic solvent extract of eucalyptus (species is not known) and Sodium alkyl sulfate (Japanese Patent Application Laid-open publication (KOKAI) No.58-39615). However, there has not been reported a combination of eucalyptus and chitosan. There have been reported a combination of an extract of eucalyptus and chitosan for a preservative for a flower (Japanese Patent Application Laid-open publication (KOKAI) No.4-316506), pesticide for plants (Japanese Patent Application Laid-open publication (KOKAI) No.7-033602). However, there has not been reported a synergy effect of antibacterial activity achieved by such a combination.

Acne is caused by propagation of *Propionibacterium acnes* present in sebaceous crypt. Athlete's foot is caused by infection with *Trichophyton mentagrophytes*. Accordingly, if *Propionibacterium acnes* and *Trichophyton mentagrophytes* can be sterilized efficiently, an acne and athlete's foot can be prevented.

Recently, hospital acquired infection caused by pathogenic bacterium such as MRSA (methicillin-resistant *Staphylococcus aureus*), VRE (vancomycin-resistant Enterococcus) or the like has been increased at medical facilities and old-age homes. Accordingly, it is an urgent subject to sterilize this pathogenic bacterium efficiently.

In an abattoir, there is a problem of contamination of apparatuses (a mincing machine, a silent cutter, a slicer, mixer, filler, a meat dehydration machine or the like) and facilities for processing meat with food poisoning bacterium such as *Escherichia coli, Salmonella enteritidis, Staphylococcus aureus* or the like.

In a conventional abattoir, sodium hypochlorite is used as a bactericide during a sterilizing process of meat. Namely, meat such as carcass (dressed carcass) is immersed in a solution of sodium hypochlorite for a certain time. However, according to the method, there is caused a chemical reaction of sodium hypochlorite and proteins in meat or gravy seeping from meat, resulting in lowering or vanishment of a bactericidal effect. Furthermore, there is a problem of safety for a human body of reaction products of sodium hypochlorite adhering to meat.

For the above-mentioned reasons, there has been requested a bactericide that has a bactericidal power that is not lowered during sterilization of meat, high safety for a human body, and a long lasting bactericidal power. Such a bactericide will keep meat fresh for a long time, and make it possible to decrease or prevent degradation of products in transit.

Furthermore, prevention of contamination in an abattoir can also be achieved by reducing contamination of livestock itself with pathogenic bacteria or fungus. One of the methods comprises sterilization of a cattle shed. *Escherichia coli* that is especially problematic, lives in livestock such as cattle, sheep, pig or the like. Especially, a cattle is contaminated at higher rate. Furthermore, *Salmonella enteritidis* is also problematic, spreading through chickens or eggs of hens. For example, if a cattle shed is contaminated with pathogenic microbe, contamination may be enlarged through livestock or hands of people who touch the livestock or the like in a cattle shed. Accordingly, it is also important to sterilize a cattle shed in order to prevent pathogenic microbe efficiently.

In stockyard for cattle, pig, chicken or the like, there occur problems such as contamination of fodder with bacteria, propagation of the bacteria in fodder or the like. If fodder is contaminated with bacteria, not only it is harmful for animals, but also contamination may be enlarged through excrementum of the animal as a source of contamination. Conventionally, fodder to which antibiotics were added were invented in order to hasten growth of animals. However, there are problems of appearance of resistant bacterium or residual antibiotics, and thus use of antibiotics is now restricted. Antibiotics are used also for fish to prevent or treat infection of pathogenic bacterium, and it is also problematic.

Recently, incidence of food poison, especially those caused by salmonella, has been increased year by year, in eggs of hen or processed foods of eggs. It is possible to decrease or prevent the contamination by sterilizing shell of eggs.

It is reported that urea-splitting bacterium is relevant to diaper rash. Accordingly, it is assumed that diaper rash can be decreased or prevented by mixing bactericide (or a fungicide) into a diaper.

As bactericides against various bacteria mentioned above, there are used alcohol, synthetic bactericides, chloric agent such as sodium hypochlorite or the like. Alcohol has a problem of insufficient persistency of bactericidal power. Synthetic bactericides and chloric agents have problem of a lack of safety for a human body. Highly safe bactericides against the above-mentioned pathogenic microbe are requested, since they may be in contact with skin of human or animals, or orally ingested.

Accordingly, an object of the present invention is to provide a bactericide (and a fungicide) that is highly safe and has strong bactericidal power against the above-mentioned pathogenic microbe even when used in low concentration, which is not reduced during a sterilizing process of meat, and that can be used repeatedly in a sterilizing process.

DISCLOSURE OF THE INVENTION

The inventors of the present invention have found that a bactericide (and a fungicide) containing a polar organic solvent extract of eucalyptus and chitosan has a strong bactericidal (or fungicidal) power in low concentration due to a synergy effect of extract of eucalyptus and chitosan, and also it has bactericidal (or fungicidal) power that can last for a long time, and is not lowered when used as a bactericide for meat (including meat products such as ham, sausage or the like). Furthermore, it has been found that, when glycerol fatty acid ester is added to the bactericide (and a fungicide) having the above-mentioned components, persistency of the bactericidal (or fungicidal) power is improved, and antifungal power of glycerol fatty acid ester is enhanced.

Namely, the present invention relates to a bactericide (and a fungicide) basically comprising a polar solvent extract of leaves of eucalyptus plants and chitosan, and if desired, additionally containing glycerol fatty acid ester, wherein the polar solvent is chosen from the group consisting of lower alcohols and glycols. Especially, the polar solvent extract of leaves of eucalyptus plant is a fraction extracted by extraction into a polar organic solvent from leaves of eucalyptus plants wherein essential oil is previously removed by degreasing with a non-polar organic solvent or steam distillation. Examples of the polar organic solvent used herein include: solvent chosen from the group consisting of halogenated hydrocarbon, ethers, fatty acid esters, ketones and lower alcohols or a mixture thereof. Example of the above-mentioned non-polar organic solvent can be alkanes.

An example of an extract from leaves of eucalyptus plant into a polar solvent can be the extract containing as a major bactericidal (or fungicidal) component a dihydrochalcone compound represented by the following formula (I):

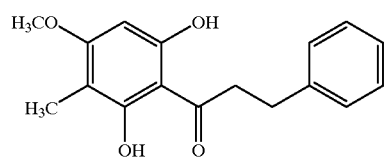

(I)

The bactericide (and the fungicide) of the present invention can be used for sterilizing medical facilities, abattoir facilities, cattle sheds, chicken houses, egg shells, meat or the like. It can also be used for affording bactericidal power to fodder, wet tissue paper, diaper or the like by mixing it therein.

The bactericide (and the fungicide) of the present invention is highly safe for human body, since it contains as active ingredients natural products that are known to be safe.

The word "sterilizing" in the present invention means both of killing microbes such as bacteria and inhibiting propagation thereof. The word "abattoir facilities" means equipment or apparatuses installed in an abattoir, as well as cooking devices such as cutlery or the like, table or the like used for processing meat.

BEST MODE FOR CARRYING OUT THE INVENTION

The present invention will be explained below in more detail.

(1) Polar Organic Solvent Extract of Eucalyptus Plants

A polar organic solvent extract of eucalyptus used for the bactericide (and the fungicide) of the present invention (hereunder referred to as "eucalyptus extract") is an extract obtained by extraction from leaves of eucalyptus plants into a polar organic solvent.

Leaves to be used as a raw material can be any leaves of plants belonged to eucalyptus, for example, *Eucalyptus grandis, Eucalyptus botryoides, Eucalyptus globulus, Eucalyptus camaldulensis, Eucalyptus crebra, Eucalyptus maculata, Eucalyptus viminalis* or the like. These leaves of eucalyptus can be those obtained from only one specie of the plants, or those obtained from two or more species of the plants.

Extraction from such leaves of eucalyptus plants is conducted with a polar organic solvent. The leaves are subjected to preliminary treatment, for example crashing of leaves to a suitable size, powdering of them, or the like, so that solvent extraction can be easily conducted. Examples of the polar organic solvent include: halogenated hydrocarbons such as chloroform, dichloro methane, dichloro ethane, trichloro ethane, or the like; ethers such as methyl ether, ethyl ether, tetrahydrofuran, dioxane or the like; esters of lower fatty acids such as methyl acetate, ethyl acetate, butyl acetate or the like; ketones such as acetone, methyl ethyl ketone or the like; lower alcohols such as methanol, ethanol, propanol or the like; glycols such as propylene glycol, butylene glycol or the like. These solvents can be alone or as a mixed solvent consisting of two, three or more kinds of any solvents. Among of the above solvents, ethyl acetate, acetone, ethanol, propylene glycol, butylene glycol are preferable, and ethanol or propylene glycol are more preferable, from the standpoint of the bactericidal activity of the resultant extract.

The method for extraction can be any methods generally conducted, including a method consisting of immersing leaves of eucalyptus as a raw material in a polar organic solvent for a long time, a method consisting of heating the leaves in a polar organic solvent with stirring at a temperature not higher than a boiling point of the polar organic solvent, and filtrating it to obtain the extract. The extract thus obtained is preferably concentrated by vacuum concentration or the like.

In order to obtain an eucalyptus extract having high bactericidal activity, the above-mentioned operation of extraction and separation are preferably conducted, not by direct extraction from leaves of eucalyptus into a polar organic solvent, but by drying the leaves of eucalyptus, degreasing them with a non-polar organic solvent to remove essential oil, and extracting the component from them into a polar organic solvent. Essential oil is removed in a process of degreasing with non-polar organic solvent. Such an operation can also be conducted by adding a polar solvent for extraction to a residue after removing essential oil by steam distillation. The above mentioned non-polar solvent can be alkanes such as hexane, pentane, heptane or the like.

However, the degreasing operation is not essential for the present invention. A fraction obtained by directly extraction from leaves of eucalyptus plant into a polar organic solvent can also be used as a bactericide (or a fungicide) of the present invention. In that case, a polar organic solvent can be lower alcohols, or glycols such as propylene glycol, butylene glycol or the like.

Comprehensively appreciating the bactericidal activity of extract of eucalyptus leaves and yield thereof, a method that can provide an extract having a strong bactericidal activity and enable high yield of the extract is a method wherein hexane is used as a non-polar solvent for degreasing, and ethanol is used as a solvent for extraction.

An extract of leaves of *Eucalyptus maculata* contains as a bactericidal compound a novel dihydrochalcone compound represented by the formula (I) shown above and known flavone compounds (eucalyptin and 8-desmethyl-eucalyptin) (Aust. J. Chem. 17, 692, 1964; Aust. J. Chem. 17, 464, 1964)). It is assumed that these compounds or analogues thereof may be used as an index in preparation of an extract of eucalyptus used for the present invention, although other compounds having a bactericidal activity may be contained in leaves of eucalyptus. As an embodiment of the extract of eucalyptus used for the present invention, there can be exemplified an extract containing at least one or more kinds of the above-mentioned dihydrochalcone compound, flavone compounds or analogues thereof as main bactericidal components, and purified compounds and analogues thereof.

(2) Chitosan

Chitosan (polyβ-1,4-glucosamin) is deacetylated chitin, which can be obtained, for example, by deacetylating chitin contained in a carapace of crustacean such as a crab, a lobster or the like, exoskeleton of insects in high concentration hot alkali solution. Alternatively, chitosan can also be obtained by culturing chitosan producing bacterium. Chitosan is also commercially available.

Molecular weight of chitosan used in the present invention is not limited, but preferably it has low viscosity, as about 5 to 50 cp (0.5% chitosan concentration). Chitosan derivatives of which aqueous solubility is increased, such as chitosan oligosaccharide, chitosan lactate, chitosan chloride or the like can also be used. However, in order to prepare a bactericide (or a fungicide) having a strong bactericidal (or a fungicidal) activity, chitosan is preferably used.

(3) Composition

The content of the above-mentioned eucalyptus extract and chitosan can be varied suitably depending on a way of use or a dosage form thereof. For example, the content of them in total is 0.0001 to 10% by weight, preferably 0.001 to 1.0% by weight. When non-volatile glycols such as propylene glycol, butylene glycol or the like are used as a solvent for extraction from leaves of eucalyptus, an eucalyptus extract is contained, for example, at a concentration of 0.1 to 10% by volume. At a higher concentration, aroma of a bactericide (or a fungicide) is adversely affected. At a lower concentration, sufficient effect is hardly achieved. Accordingly, the above-mentioned range is preferable. Eucalyptus extract and chitosan can be mixed at any ratio as far as a concentration thereof is in the above-mentioned range. Acids for dissolving chitosan (lactic acid, acetic acid or the like) can be added at any concentration so that chitosan can be dissolved.

(4) Bactericide (and a fungicide) to which Glycerol Fatty Acid Ester is Added

According to the present invention, glycerol fatty acid ester can be added to the above-mentioned bactericide (and a fungicide) having a composition comprising eucalyptus extract and chitosan. In that case, 0.0001 to 20% by weight, preferably 0.001 to 1.0% by weight of glycerol fatty acid ester can be added to the above-mentioned composition comprising eucalyptus extract and chitosan.

When the above-mentioned bactericide is used as a bactericide for meat, components seeping from meat during sterilization increase pH of the bactericide. If pH is more than 5.5, a bactericidal power is lowered. Accordingly, acids such as lactic acid, acetic acid or the like or a pH control agent are added to maintain pH to be 5.5 or less, preferably 5.0 or less. The acids or the pH control agents can be added in advance to the bactericide at high concentration, or the acids can be continuously added during sterilization to maintain pH to be 5.5 or less.

There can be mixed in the bactericide (and a fungicide) of the present invention other components that are generally used for foods, pharmaceuticals, quasi-drugs, cosmetics or the like, acidity control agents, stabilizers, surfactants, antioxidants or the like, as far as the effect of the present invention is not deteriorated, and two or more of the components can be mixed therein. Furthermore, the bactericide (and a fungicide) of the present invention can be used together with other bactericides (or fungicides) to enhance bactericidal (or fungicidal) effect.

Examples of the components generally used for foods, pharmaceuticals, quasi-drugs, cosmetics or the like include: surfactants (anionic, cationic, ampholytic surfactants or nonionic surfactants), antioxidant (stearate, nordihydro guasereten acid, dibutyl hydroxyl toluene, butyl hydroxy anisole, p-hydroxyl anisole, propyl gallate, sesamol, sesamolin, gossypol or the like), humectant (propylene glycol, 1,3-butylene glycol, polyethylene glycol, glycerin, chondroitin sulfuric acid and salt thereof, hyaluronic acid and salt thereof, sodium lactate, royal jelly extract or the like). Furthermore, collagen, lower alcohols, polyhydric alcohols, water soluble polymers, pH control agents, flavoring agents, restorative agents, stabilizers, extracts of animals or plants, proteins of animals or plants and decomposed products thereof, polysaccharides of animals or plants and a decomposed products thereof, glycoproteins of animals or plants and decomposed products thereof, microorganism culture metabolites, amino acids and salts thereof, deodorizing agents, emulsifying agents can also be mixed therein and used.

Examples of the acidity controls and the stabilizers for the functions include: adipic acid, citric acid, sodium citrate, glycine, fatty acid glyceride, glucono-δ-lactone, gluconic acid, succinic acid, sodium hydrogen succinate, sodium succinate, acetic acid, sodium acetate, DL-tartaric acid, L-tartaric acid, DL-sodium tartrate, L-sodium tartrate, carbonates, carbon dioxide, lactic acid, sodium lactate, fumaric acid, monosodium fumarate, lysozyme, DL-malic acid, DL-sodium malate, phosphoric acid, phosphates, polymerized phosphates, itaconic acid, phytic acid and the like.

Examples of the surfactants include: fatty acid esters such as glycerol monostearate, trioleic acid polyglycerol or the like, organic acid monoglyceride, propylene glycol fatty acid ester, sorbitan fatty acid ester, sugar fatty acid ester, lecithin, lysolecithin, polyethylene glycol, polyoxy alkyl ether, polyoxy ethylene polyamine, alkyl polyoxy ethylene sulfate, a salt of alkyl sulfate ester, a salt of acyl methyl taurine, N-acyl glutamate, alkyl amide betain and the like.

Examples of the antioxidants include catechin, tocopherol, propolis, ellagic acid, extracts of animals or plants (sage, The Japanese parsley, rosemary or the like).

Examples of the bactericides include any of substances or extracts having bactericidal activity, such as hinokitiol, triclosan, cetylpyridinium chloride, chlorhexidine gluconate, extracts of animals or plants, essential oils or the like.

As described above, due to the synergistic effect of the eucalyptus extract and chitosan, the bactericide containing eucalyptus plant extract and chitosan has a strong bactericidal power against methicillin-resistant *Staphylococcus aureus*(MRSA), *Staphylococcu aureus, Escherichia coli, Salmonella typhimurium, Salmonella enteritidis, Enterococcus faecalis, Pseudomonas putida, Bacillus subtilis, Bacillus cereus, Vibrio parahaemolyticus, Arthrobacter globiformis, Brevibacterium linens, Proteus vulgaris, Propionobacterium acnes, Trichophyton mentagrphytes*, and the bactericidal power is persistent. Both of the eucalyptus extract and chitosan have high safety. Accordingly, if ingredients having high safety are chosen as the other ingredients, a bactericide having high safety can be provided.

The fungicide wherein glycerol fatty acid ester is added to the composition containing the above-mentioned eucalyptus extract and chitosan may have an effect against fungi such as *Aspergillus niger, Penicillium citrinum* or the like, due to the synergistic effect of the eucalyptus extract and glycerol fatty acid ester. If the fungicide of the present invention is prepared as a mixture in ethanol and water, an effect to the above fungi can also be achieved, since an instantaneous bactericidal power of ethanol is afforded thereto.

(5) Utility

The preparation form of the bactericide (and fungicide) of the present invention is not limited. It can be selected depending on an application form such as a liquid agent, a spray agent, a paste agent, a mousse agent or the like. It can also be defined appropriately depending on an application method such as spraying, dipping, coating, wiping-up or the like. The bactericide (or a fungicide) may be a spray agent. It can be used at a kitchen of restaurants or general home or the like. When it is in the form of liquid, an eucalyptus extract and chitosan are dissolved in suitable solvent to provide a bactericide (or a fungicide) solution. Examples of the solvent include: mixture of ethanol and water (at any mixing ratio) to which an acid such as lactic acid, acetic acid is added in order to dissolve chitosan. However, when the bactericide is used as a bactericide for meats, concentration of alcohol is preferably in the range of about 0 to 10%, since an alcohol at high concentration may denature proteins. The above-mentioned acid is not necessary to be used, when chitosan oligosaccharides having an increased water solubility or chitosan derivatives having an increased water solubility are used.

In the case that the bactericide of the present invention is used in a step of sterilizing meat, it can be used repeatedly in the sterilizing step, since a bactericidal power thereof is not lowered. If the bactericide is used for sterilizing treatment of meat, it can keep meat fresh for a long time, since it can inhibit propagation of the bacterium on the surface of the meat for a long time.

When the bactericide is used as a bactericide of egg shells of birds, the eggs on which the bactericide of the present invention is adhered can be distributed.

When the bactericide (or the fungicide) is used as spray agents, the storage containers can be those enabling sparay of the bactericide. For example, it is the sprayer container due to aerosol method, trigger method or the like. When the container of aerosol method is used, an agent for spraying like carbonic acid gas, nitrogen gas or dimethyl ether is added.

EXAMPLES

The present invention will be hereunder explained more in detail in the following Examples and Comparative Examples. These examples are only for illustrating the present invention. The scope of the present invention is defined only by claims.

Preparation Example 1

Leaves of eucalyptus (*Eucalyptus grandis, Eucalyptus botryoides, Eucalyptus globulus, Eucalyptus camaldulensis, Eucalyptus crebra, Eucalyptus maculata, Eucalyptus viminalis*) were dried (a dry weight of each of plants was 30 g). Extraction from each of them into 500 ml of acetone was conducted at room temperature over three days. Solvent was removed from each of the extracts by evaporation under reduced pressure to provide an acetone extract.

Preparation Example 2

Leaves of eucalyptus (*Eucalyptus grandis, Eucalyptus botryoides, Eucalyptus globulus, Eucalyptus camaldulensis, Eucalyptus crebra, Eucalyptus maculata, Eucalyptus viminalis*) were dried (a dry weight of each of plants was 30 g). Extraction from each of them into 500 ml of ethanol was conducted at room temperature over three days. Solvent was removed from each of the extracts by evaporation under reduced pressure to provide an ethanol extract.

Preparation Example 3

Leaves of eucalyptus (*Eucalyptus grandis, Eucalyptus botryoides, Eucalyptus globulus, Eucalyptus camaldulensis, Eucalyptus crebra, Eucalyptus maculata, Eucalyptus viminalis*) were dried (a dry weight of each of plants was 30 g). Each of them was degreased with 500 ml of n-hexane at room temperature over two days, and extraction therefrom into 500 ml of ethanol was conducted at room temperature over three days. Solvent was removed from each of the extracts by evaporation under reduced pressure to provide an ethanol extract.

Preparation Example 4

Leaves of eucalyptus (*Eucalyptus maculata*) were dried (a dry weight was 500 g), and degreased with 6 l of n-hexane at room temperature over two days, and then extraction therefrom into 6 l of acetone was conducted at room temperature over three days. Solvent was removed from the extracts by evaporation under reduced pressure to provide about 65 g of an acetone extract. Yield calculated based on the leaves was 13%.

Preparation Example 5

Leaves of eucalyptus (*Eucalyptus grandis, Eucalyptus botryoides, Eucalyptus globulus, Eucalyptus camaldulensis, Eucalyptus crebra, Eucalyptus maculata, Eucalyptus viminalis*) were dried (a dry weight of each of plants was 30 g). Extraction from them into 500 ml of propylene glycol was conducted at room temperature over three days.

Preparation Example 6

Leaves of eucalyptus (*Eucalyptus grandis, Eucalyptus botryoides, Eucalyptus globulus, Eucalyptus camaldulensis, Eucalyptus crebra, Eucalyptus maculata, Eucalyptus viminalis*) were dried (a dry weight of each of plants was 30 g). Extraction from them into 500 ml of 1,3-butylene glycol was conducted at room temperature over three days.

The resultant acetone extract was subjected to partition between hexane and water. After removal of hexane layer, the remaining water layer was subjected to partition between dichloromethane and water, subsequently to partition between ethyl acetate and water, and then to partition between n-butanol and water. The resultant ethyl acetate fraction as a highly active fraction was concentrated to yield 23 g of ethyl acetate extract (yield based on the leaves was 4.6%).

Then, the ethyl acetate fraction was subjected to silica gel column chlomatography using hexan —ethyl acetate mixture as an eluent. The fraction eluted with hexane/ethyl acetate=⅕ mixture was concetrated to provide 3.92 g of active fraction (yield based on the leaves was 0.78%). The fraction was then subjected to ODS-HPLC. The fraction eluted with hexane/ethyl acetate=3/1 mixture was concentrated to yield 3.92 g of an active fraction (yield based on the leaves was 0.78%). The fraction was then subjected to ODS-HPLC, with a mixture of methanol/distilled water=80/20, yielding 1.33 g of Compound (I) (content in leaves was 0.27%), 156 mg of Compound (II) (content in leaves was 0.031%), 125 mg of Compound (III) (content in leaves was 0.025%).

It was found that Compound (II) and Compound (III) were respectively eucalyptin and 8-desmethyl-eucalyptin that are known flavone compounds (Aust. J. Chem. 17, 692, 1964; Aust. J. Chem. 17, 464, 1964).

As shown in the following physical data, Compound (I) was a novel dihydrochalcone compound.

Molecular weight: EI-MS m/z 286(M+), 181, 154,
Molecular formula: $C_{17}H_{18}O_4$
UV ($\lambda_{max}$ MeOH): 286 nm($\epsilon$=21700); IR ($\nu_{max}$ KBr): 3296, 2944, 2924, 1650, 1595, 1516, 1429, 1274, 1247, 1213, 1147, 1112, 1082, 886, 799, 742, 720, 699, 468 cm$^{-1}$
$^1$H-NMR ($\delta$DMSO-d$_6$): 1.86(3H, s), 2.89(1H, t, J=7.6), 3.32(1 H, t, J=7.6), 3.77(3H, s), 6.08(1H, s), 7.15–7.30(5H, m), 10.92(1H, s), 13.64(1H, s)ppm; $^{13}$C-NMR ($\delta$DMSO-d$_6$): 7.2, 30.1, 45.3, 55.4, 90.3, 102.3, 104.1, 125.8, 128.3, 141.6, 160.5, 162.0, 163.2, 204.7 ppm.

[Antibacterial (or antifungal) Activity of an Eucalyptus Extract and Chitosan]

(1) The Eucalyptus Extract Obtained in Preparation Example 3 and Chitosan were Examined for Antibacterial (or antifungal) Activity Using the Following Bacterium and Fungus:

MRSA RIM 0310925, Staphylococcus aureus IF012732, Escherichia coli IF012734, Salmonella typhimurium IF012529, Salmonella enteritidis IF03313, Enterococcus faecalis IF012970, Pseudomonas putida IF03738, Bacillus subtilis JCM1465, Bacillus cereus IF03001, Vibrio parahaemolyticus IF012711, Arthrobacter globiformis IF012137, Brevibacterium linens IF012142, Proteus vulgaris IF030456, Propionibacterium acnes ATCC6919, Trichophyton mentagrophytes IF005466

Each of the strains was previously cultured under the culture condition shown in Table 1, diluted with physiological saline, so that the number of bacteria was about $5 \times 10^8$/ml in the case of bacterium, and the number of spores was $5 \times 10^6$/ml in the case of fungus (Trichophyton mentagrophytes). Propionibacterium acnes were cultured under anaerobic condition.

TABLE 1

| | Culture condition | | |
|---|---|---|---|
| Strain | Medium | Culture temperature | Culture time |
| MRSA | Nutrient | 37° C. | 24 hr |
| Staphylococcus aureus | Nutrient | 37° C. | 24 hr |
| Escherichia coli | Nutrient | 37° C. | 24 hr |
| Salmonella typhimurium | Nutrient | 28° C. | 24 hr |
| Salmonella enteritidis | Nutrient | 28° C. | 24 hr |
| Enterococcus faecalis | BHI | 37° C. | 24 hr |
| Pseudomonas putida | Nutrient | 28° C. | 24 hr |
| Bacillus subtilus | Nutrient | 28° C. | 24 hr |
| Bacillu cereus | Nutrient | 28° C. | 24 hr |
| Vibrio parahaemolyticus | Nutrient | 37° C. | 24 hr |
| Arthrobacter globiformis | Nutrient | 28° C. | 24 hr |
| Brevibacterium linens | Nutrient | 28° C. | 24 hr |
| Proteus vulgaris | Nutrient | 28° C. | 24 hr |
| Propionibacterium acnes | Tripticase soy | 37° C. | 24 hr |
| Trichophyton mentagrophytes | Sabouraud's glucose | 28° C. | 7 days |

The eucalyptus extract obtained in Preparation Example 3 was dissolved in DMSO. Then, 10 μl of the solution was added to 190 μl of culture medium in each well of 96 well plate so that the final concentration of the extract was 63 to 0.2 μg/ml. Chitosan (Wako Junyaku corporation: Chitosan 10) was dissolved in sterilized water (to which 0.005% of lactic acid was added, pH 5.3), and then the solution was added to 190 μl of culture medium in each well of 96 well plate so that the final concentration of chitosan was 63 to 0.2 μg/ml. Finally, 10 μl of the above-mentioned bacteria suspension was added to each well, cultured under the condition suitable for culture of each strain shown in Table 1. Development was observed with naked eyes after 24 hours as for bacterium, and after 7 days as for fungus (Trichophyton mentagrophytes), to determine minimum inhibitory concentration (MIC).

Table 2 shows MIC of each of eucalyptus extracts and chitosan. Eucalyptus extracts had especially strong antibacterial activities against MRSA, Staphylococcus aureus, Enterococcus faecalis, Pseudomonas putida, Bacillus subtilis, Bacillus cereus, Arthrobacter globiformis, Propionibacterium acnes, and antifungal activities against Trichophyton mentagrophytes, and had apparently different antibacterial spectum from that of chitosan.

TABLE 2

Minimum inhibitory concentration of eucalyptus extracts and chitosan

| | Minimum inhibitory concentration: MIC (μg/ml) | | | | | | | |
|---|---|---|---|---|---|---|---|---|
| Strain | E. gra | E. bot | E. glo | E. cam | E. cre | E. mac | E. vim | Chitosan |
| MRSA | 15.6 | 31 | 3.9 | 15.6 | 63 | 7.8 | 7.8 | 63 |
| Staphylococcus aureus | 15.6 | 31 | 3.9 | 15.6 | 63 | 3.9 | 3.9 | 31 |
| Escherichia coli | 63 | >63 | >63 | >63 | >63 | >63 | >63 | 31 |

TABLE 2-continued

Minimum inhibitory concentration of eucalyptus extracts and chitosan

Minimum inhibitory concentration: MIC (μg/ml)

| Strain | E. gra | E. bot | E. glo | E. cam | E. cre | E. mac | E. vim | Chitosan |
|---|---|---|---|---|---|---|---|---|
| Salmonella typhimurium | 63 | >63 | >63 | >63 | >63 | >63 | >63 | 31 |
| Salmonella enteritidis | 63 | >63 | >63 | >63 | >63 | 63 | >63 | 63 |
| Enterococcus faecalis | 31 | 31 | 15.6 | >63 | 63 | 15.6 | 15.6 | >63 |
| Pseudomonas putida | 63 | 31 | 63 | 63 | >63 | >63 | 63 | 63 |
| Bacillus subtilis | 31 | >63 | 7.8 | >63 | 31 | 3.9 | 7.8 | 31 |
| Bacillus cereus | 15.6 | 63 | 2 | 63 | 15.6 | 2 | 2 | 63 |
| Vibrio parahaemolyticus | 63 | >63 | >63 | >63 | >63 | 63 | 63 | 31 |
| Arthrobacter globiformis | 7.8 | 2 | 3.9 | 15.6 | 3.9 | 1 | 3.9 | 31 |
| Brevibacterium linens | 3.9 | 2 | 2 | 15.6 | 3.9 | 2 | 3.9 | 15.6 |
| Proteus vulgaris | >63 | >63 | >63 | >63 | >63 | >63 | >63 | 31 |
| Propionibacterium acnes | 63 | 15.6 | 7.8 | 63 | 31 | 15.6 | 7.8 | 63 |
| Trichophyton mentagrophytes | 15.6 | 15.6 | 31 | 31 | 7.8 | 7.8 | 15.6 | >63 |

E. gra: E. grandis,
E. bot: E. botryoides,
E. glo: E. globulus,
E. cam: E. camaldulensis,
E. cre: E. crebra,
E. mac: E. maculata,
E. vim: E. viminalis In order to evaluate antibacterial (or antifungal) activities of essential oils, essential oils were obtained from leaves of eucalyptus plants by steam distillation. Minimum inhibitory concentration thereof against each of bacteria (or fungus) was determined according to a similar method to the above-mentioned method. Ethanol was used as a solvent for dissolving essential oils.

MIC values of essential oils obtained from eucalyptus were shown in Table 3. As shown in Table 3, it was found that essential oils did not have strong antibacterial (or antifungal) activities.

(2) The Eucalyptus Extract Obtained in Preparation Example 5 was Examined for Antibacterial Activities According to the Following Method.

The eucalyptus extracts prepared in Example 5 were diluted 10 times with sterilized distilled water. 10 μl of the dilution was added to 190 μl of medium shown in Table 1 in each well of 96 well plate (the extract was diluted 200 times). The antibacterial activities and antifungal activities were evaluated according to the similar method to the above-mentioned method.

The results are shown in Table 4. As shown in the table, the extracts (200 times dilution)had antibacterial activities

TABLE 3

Minimum inhibitory concentration of eucalyptus essential oils

Minimum inhibitory concentration: MIC (μg/ml)

| Strain | E. gra | E. bot | E. glo | E. cam | E. cre | E. mac | E. vim |
|---|---|---|---|---|---|---|---|
| MRSA | >63 | >63 | >63 | >63 | >63 | >63 | >63 |
| Staphylococcus aureus | >63 | >63 | >63 | >63 | >63 | >63 | >63 |
| Escherichia coli | >63 | >63 | >63 | >63 | >63 | >63 | >63 |
| Salmonella typhimurium | >63 | >63 | >63 | >63 | >63 | >63 | >63 |
| Salmonella enteritidis | >63 | >63 | >63 | >63 | >63 | >63 | >63 |
| Enterococcus faecalis | >63 | >63 | >63 | >63 | >63 | >63 | >63 |
| Pseudomonas putida | >63 | >63 | >63 | >63 | >63 | >63 | >63 |
| Bacillus subtilis | >63 | >63 | >63 | >63 | >63 | >63 | >63 |
| Bacillus cereus | >63 | >63 | >63 | >63 | >63 | >63 | >63 |
| Vibrio parahaemolyticus | >63 | >63 | >63 | >63 | >63 | >63 | >63 |
| Arthrobacter globiformis | >63 | >63 | >63 | >63 | >63 | >63 | >63 |
| Brevibacterium linens | >63 | >63 | >63 | >63 | >63 | >63 | >63 |
| Proteus vulgaris | >63 | >63 | >63 | >63 | >63 | >63 | >63 |
| Propionibacterium acnes | >63 | >63 | >63 | >63 | >63 | >63 | >63 |
| Trichophyton mentagrophytes | >63 | >63 | >63 | >63 | >63 | >63 | >63 |

E. gra: E. grandis,
E. bot: E. botryoides,
E. glo: E. globulus,
E. cam: E. camaldulensis,
E. cre: E. crebra,
E. mac: E. maculata,
E. vim: E. viminalis against MRSA, *Staphylococcus aureus*, *Enterococcus faecalis*, *Pseudomonas putida*, *Bacillus subtilis*, *Bacillus cereus*, *Arthrobacter globiformis*, *Propionibacterium acnes*, and antifungal activity against *Trichophyton mentagrophytes*.

namely synergic effect was achieved. (FIC index=MBC of A component when used together with component B/MBC of A component+MBC of B component when used together with component A/MBC of B component: see 25th Nihon Boukinboukabigakkai Nenjitaikai p.35).

TABLE 4

Antibacterial activities of propylene glycol extracts of eucalyptus

| Strain | Antibacterial activity | | | | | | |
|---|---|---|---|---|---|---|---|
| | E. gra | E. bot | E. glo | E. cam | E. cre | E. mac | E. vim |
| MRSA | + | + | + | + | + | + | + |
| Staphylococcus aureus | + | + | + | + | + | + | + |
| Escherichia coli | − | − | − | − | − | − | − |
| Salmonella typhimurium | − | − | − | − | − | − | − |
| Salmonella enteritidis | − | − | − | − | − | − | − |
| Enterococcus faecalis | + | + | + | − | − | + | + |
| Pseudomonas putida | + | + | + | + | − | − | + |
| Bacillus subtilus | + | − | + | − | + | + | + |
| Bacillus cereus | + | − | + | − | + | + | + |
| Vibrio parahaemolyticus | − | − | − | − | − | + | + |
| Arthrobacter globiformis | + | + | + | + | + | + | + |
| Brevibacterium linens | + | + | + | + | + | + | + |
| Proteus vulgaris | − | − | − | − | − | − | − |
| Propionibacterium acnes | + | + | + | + | + | + | + |
| Trichophyton mentagrophytes | + | + | + | + | + | + | + |

E. gra: E. grandis,
E. bot: E. botryoides,
E. glo: E. globulus,
E. cam: E. camaldulensis,
E. cre: E. crebra,
E. mac: E. maculata,
E. vim: E. viminalis
+ active;
− no activity

[Test of Antibacterial Power when Both of Eucalyptus Extract and Chitosan were Used]

Eucalyptus extract prepared in Preparation Example 2 was dissolved in DMSO to make double dilution series. Chitosan was dissolved in sterilized water (to which lactic acid was added). 50 μl each of the solutions were mixed with 900 μl of sterilized distilled water (final concentration of eucalyptus extract: 0 to 2500 μg/ml; final concentration of chitosan: 0 to 125 μg/ml; lactic acid concentration: 3/5% by volume per 1% by weight of chitosan).

Then, each of bacteria MARSA RIM0310925 *Bacillus subtilin* JCM1465, *Escherichia coli* IFO 12734) was cultured and then added to the above-mentioned mixture, and then left for one hour as for MRSA, *B. Subtilin*, and for 4 hours as for *E. coli*. After allowed to stand, 1 ml of the solution was added to 15 ml of nutrient agar medium, cultured under the condition suitable for each bacteria for 24 hours. Growth of each bacteria was observed (+: growth was observed; −: growth was not observed).

The result as for MRSA was shown in Table 5. As shown in the table, when both 1.0 μg/ml of eucalyptus extract and 3.1 μg/ml of chitosan were used, FIC index calculated from minimum bactericidal concentration (MBC) was 0.19. Namely, a synergic effect was achieved. (FIC index of 0.5 or less means synergic effect). The result as for *B. Subtilin* was shown in Table 6. When 0.5 μg/ml of eucalyptus extract and 3.1 μg/ml of chitosan were used, FIC Index was 0.312, namely synergic effect was achieved. The result as for *E. coli* was shown in Table 7. When 78 μg/ml of eucalyptus extract and 7.8 μg of chitosan were used, FIC Index was 0.187,

TABLE 5

Bactericidal power when using both Eucalyptus extract and chitosan

| MRSA | Chitosan (μg/ml) | | | | | |
|---|---|---|---|---|---|---|
| | 0 | 3.1 | 6.3 | 12.5 | 25 | 50 |
| Eycalyptus extract (μg/ml) | | | | | | |
| 125 | − | − | − | − | − | − |
| 63 | − | − | − | − | − | − |
| 31 | − | − | − | − | − | − |
| 15.6 | − | − | − | − | − | − |
| 7.6 | − | − | − | − | − | − |
| 3.9 | + | − | − | − | − | − |
| 2.0 | + | − | − | − | − | − |
| 1.0 | + | − | − | − | − | − |
| 0.5 | + | + | − | − | − | − |
| 0 | + | + | + | + | + | − |

+ bacteria were grown,
− bacteria were not grown

TABLE 6

Bactericidal power when using both Eucalyptus extract and chitosan

| Bacillus subtilus | Chitosan (μg/ml) | | | | | |
|---|---|---|---|---|---|---|
| | 0 | 3.1 | 6.3 | 12.5 | 25 | 50 |
| Eycalyptus extract (μg/ml) | | | | | | |
| 125 | − | − | − | − | − | − |
| 63 | − | − | − | − | − | − |

TABLE 6-continued

Bactericidal power when using both Eucalyptus extract and chitosan

| Bacillus subtilus | Chitosan (μg/ml) | | | | | |
|---|---|---|---|---|---|---|
| | 0 | 3.1 | 6.3 | 12.5 | 25 | 50 |
| 31 | − | − | − | − | − | − |
| 15.6 | − | − | − | − | − | − |
| 7.6 | − | − | − | − | − | − |
| 3.9 | − | − | − | − | − | − |
| 2.0 | − | − | − | − | − | − |
| 1.0 | + | − | − | − | − | − |
| 0.5 | + | − | − | − | − | − |
| 0.24 | + | + | + | − | − | − |
| 0 | + | + | + | + | + | − |

+ bacteria were grown,
− bacteria were not grown

TABLE 7

Bactericidal power when using both Eucalyptus extract and chitosan

| E. coli | Chitosan (μg/ml) | | | | | | | |
|---|---|---|---|---|---|---|---|---|
| | 0 | 2.0 | 3.9 | 7.8 | 15.6 | 31.3 | 62.5 | 125 |
| Eycalyptus extract (μg/ml) | | | | | | | | |
| 2500 | − | − | − | − | − | − | − | − |
| 1250 | − | − | − | − | − | − | − | − |
| 625 | + | − | − | − | − | − | − | − |
| 313 | + | − | − | − | − | − | − | − |
| 156 | + | − | − | − | − | − | − | − |
| 78 | + | + | + | − | − | − | − | − |
| 39 | + | + | + | + | + | − | − | − |
| 19.5 | + | + | + | + | + | − | − | − |
| 0 | + | + | + | + | + | + | − | − |

+ bacteria were grown,
− bacteria were not grown

[Persistency Test of Bactericidal Power of Bactericide]

Examples 1 to 3

The eucalyptus extract prepared in Preparation example 3 and chitosan and other components were mixed at a mixing ratio shown in Table 8, to provide bactericides of Examples 1 to 3 and Comparative Examples 1 to 4. Amounts of eucalyptus extracts and chitosan were shown in % by weight, and amounts of lactic acid and ethanol were shown in % by volume.

Test Example 1: Persistency Test of Bactericidal Power on Paper

A paper disk having a diameter of 8 mm that was previously subjected to dry heat sterilization, was impregnated with 25 μl of each of bactericides shown in Table 8 and allowed to stand for 7 days. The bacteria suspension that was previously cultured under the condition shown in Table 1 was diluted with physiological saline, and then with 10 μl thereof was impregnated the paper disk. After one minute, it was immediately put into physiological saline (1 ml) in test tube, stirred for one minute with vortex stirrer to liberate bacteria from the paper disk. The resultant physiological saline was diluted, and a certain amount of the dilution was spread on an agar medium. The viable count was determined. Water was used as a control. 70% Ethanol was used as a conventional bactericide control. The results of Examples were shown in Table 9. The results of Comparative Examples were shown in Table 10. Even on 7th day after the bactericide was spread, the bactericides of Examples containing both of the eucalyptus extract and chitosan had strong bactericidal power. The bactericidal power thereof was stronger than that of bactericides containing only eucalyptus extract (Comparative Examples 1 to 3) or that containing only chitosan (Comparative Example 4).

TABLE 9

Bactericidal power of bactericides

| | Viable count (After 7 days) (Number/Disk) | | |
|---|---|---|---|
| | Example 1 | Example 2 | Example 3 |
| MRSA | <10 | <10 | <10 |
| Staphylococcus aureus | <10 | <10 | <10 |
| Escherichia coli | 10 | 10 | 30 |
| Salmonella typhimurium | 1.1 × 10² | 90 | 1.2 × 10² |
| Salmonella enteritidis | 30 | 30 | 50 |
| Pseudomonas putida | <10 | <10 | <10 |
| Bacillus subtilus | <10 | <10 | <10 |
| Bacillus cereus | <10 | <10 | <10 |
| Vibrio parahaemolyticus | <10 | <10 | <10 |
| Arthrobacter globiformis | <10 | <10 | <10 |
| Brevibacterium linens | <10 | <10 | <10 |
| Proteus vulgaris | 70 | 50 | 50 |
| Propionibacterium acnes | <10 | <10 | <10 |

TABLE 8

Composition of bactericides

| | Example 1 | Example 2 | Example 3 | Comparative Example 1 | Comparative Example 2 | Comparative Example 3 | Comparative Example 4 |
|---|---|---|---|---|---|---|---|
| Eucalyptus extract | E. vim 0.010% | E. glo 0.010% | E. mac 0.010% | E. vim 0.020% | E. glo 0.020% | E. mac 0.020% | No addition |
| Chitosan | 0.010% | 0.010% | 0.010% | No addition | No addition | No addition | 0.020% |
| Lactic acid | 0.010% | 0.010% | 0.010% | 0.010% | 0.010% | 0.010% | 0.010% |
| Ethanol | 70% | 70% | 70% | 70% | 70% | 70% | 70% |

E. vim: E. viminalis,
E. glo: E. globulus,
E. mac: E. maculata

TABLE 10

Bactericidal power of bactericides

| | Viable count (After 7 days) (Number/Disk) | | | | | |
|---|---|---|---|---|---|---|
| | Comparative Example 1 | Comparative Example 2 | Comparative Example 3 | Comparative Example 4 | 70% Ethanol | Water |
| MRSA | $7.1 \times 10^2$ | $5.2 \times 10^2$ | $6.5 \times 10^2$ | $2.8 \times 10^4$ | $3.5 \times 10^5$ | $3.5 \times 10^5$ |
| Staphylococcus aureus | $4.8 \times 10^2$ | $4.5 \times 10^2$ | $5.5 \times 10^2$ | $6.2 \times 10^3$ | $2.2 \times 10^5$ | $2.2 \times 10^5$ |
| Escherichia coli | $6.4 \times 10^3$ | $5.3 \times 10^3$ | $4.3 \times 10^3$ | $1.4 \times 10^3$ | $8.2 \times 10^5$ | $8.2 \times 10^5$ |
| Salmonella typhimurium | $8.6 \times 10^3$ | $5.0 \times 10^3$ | $5.2 \times 10^3$ | $1.2 \times 10^3$ | $2.8 \times 10^5$ | $2.8 \times 10^5$ |
| Salmonella enteritidis | $4.0 \times 10^4$ | $2.8 \times 10^4$ | $3.3 \times 10^4$ | $3.9 \times 10^3$ | $7.5 \times 10^5$ | $7.5 \times 10^5$ |
| Pseudomonas putida | $2.9 \times 10^3$ | $2.0 \times 10^3$ | $2.8 \times 10^3$ | $5.6 \times 10^3$ | $4.7 \times 10^5$ | $4.7 \times 10^5$ |
| Bacillus subtilus | $9.3 \times 10^2$ | $5.7 \times 10^2$ | $7.0 \times 10^2$ | $8.8 \times 10^4$ | $3.5 \times 10^5$ | $3.5 \times 10^5$ |
| Bacillus cereus | $7.7 \times 10^2$ | $4.0 \times 10^2$ | $4.0 \times 10^2$ | $6.2 \times 10^4$ | $4.0 \times 10^5$ | $4.0 \times 10^5$ |
| Vibrio parahaemolyticus | $1.1 \times 10^4$ | $1.3 \times 10^4$ | $9.5 \times 10^3$ | $3.1 \times 10^3$ | $3.7 \times 10^5$ | $3.7 \times 10^5$ |
| Arthrobacter globiformis | $1.3 \times 10^3$ | $8.5 \times 10^2$ | $4.6 \times 10^2$ | $6.6 \times 10^4$ | $9.5 \times 10^5$ | $9.5 \times 10^5$ |
| Brevibacterium linens | $7.4 \times 10^2$ | $5.6 \times 10^2$ | $8.8 \times 10^2$ | $4.2 \times 10^4$ | $8.4 \times 10^5$ | $8.4 \times 10^5$ |
| Proteus vulgaris | $1.4 \times 10^4$ | $7.5 \times 10^3$ | $9.2 \times 10^3$ | $4.4 \times 10^3$ | $2.7 \times 10^5$ | $2.7 \times 10^5$ |
| Propionibacterium acnes | $4.0 \times 10^2$ | $3.6 \times 10^2$ | $4.5 \times 10^2$ | $7.5 \times 10^3$ | $3.2 \times 10^5$ | $3.2 \times 10^5$ |

[Test Example 2] Test of Activity Against *Trichophyton mentagrphytes*

A paper disk having a diameter of 8 mm that was previously subjected to dry heat sterilization, was impregnated with 25 μl of each of fungicides shown in Table 8 and allowed to stand for 24 hours to be dried. The paper disk was put on agar medium on which spore suspension of *Trichophyton mentagrphytes* previously prepared was spread, and cultured at 28° C. for five days. It was observed whether a block circle (zone of inhibition) around the paper disk. 70% ethanol that was known fungicide was used as a control. As shown in Table 11, when each of the fungicides of Examples containing both of the eucalyptus extract and chitosan was used, a larger block circle was formed than that formed when a fungicide containing only eucalyptus extract was used. No block circle was formed when a fungicide containing only chitosan (Comparative Example 4) was used. Namely, it was shown that eucalyptus extract had a persistent fungicidal power against *Trichophyton mentagrphytes*, and chitosan enhanced the fungicidal power.

TABLE 11

Fungicidal activity against *Trichophyton mentagrphytes*

Diameter of block circle

| Example 1 | Example 2 | Example 3 | Comparative Example 1 | Comparative Example 2 | Comparative Example 3 | Comparative Example 4 | 70% Ethanol |
|---|---|---|---|---|---|---|---|
| 21 mm | 23 mm | 20 mm | 12 mm | 13 mm | 13 mm | None | None |

Test Example 3: Test of Persistency of Bactericidal Power on Stainless Steel

Each of bactericide shown in Table 8 was sprayed on a sterilized stainless steel plate (15 μl/cm²), and allowed to stand for seven days in a sterilized room to be dried. Each of the bacteria suspension previously cultured in a similar manner to that described above was diluted with physiological saline. Then, 10 μl of the diluted suspension was spread on the stainless steel. After allowed to stand for 10 minutes, bacterium on the stainless steel were wiped with absorbent cotton, and liberated into physiological saline. Then, visible count was counted. The results of Examples were shown in Table 12, and the results of Comparative Examples were shown in Table 13. For comparison, 70% ethanol was used as a conventional bactericide. Strong bactericidal power of each bactericide of examples containing both eucalyptus extract and chitosan was maintained, even after elapse of seven days, on the stainless steel on which it was spread. The bactericidal power was stronger than that of bactericides containing only eucalyptus extract (Comparative Examples 1 to 3) or a bactericide containing only chitosan (Comparative Example 4).

TABLE 12

Persistency of bactericidal power of bactericides

| | Viable count (After 7 days) (Number/100 cm²) | | |
|---|---|---|---|
| | Example 1 | Example 2 | Example 3 |
| MRSA | <10 | <10 | <10 |
| Staphylococcus aureus | 10 | <10 | <10 |
| Escherichia coli | 80 | 40 | 50 |

TABLE 12-continued

Persistency of bactericidal power of bactericides

| | Viable count (After 7 days) (Number/100 cm²) | | |
|---|---|---|---|
| | Example 1 | Example 2 | Example 3 |
| Bacillus subtilis | <10 | <10 | <10 |
| Salmonella enteritidis | 80 | 30 | 80 |

TABLE 13

Persistency of bactericidal power of bactericides

| | Viable count (After 7 days) (Number/100 cm$^2$) | | | | | |
|---|---|---|---|---|---|---|
| | Comparative Example 1 | Comparative Example 2 | Comparative Example 3 | Comparative Example 4 | 70% Ethanol | No treatment |
| MRSA | 7.5 × 10$^2$ | 4.6 × 10$^2$ | 6.0 × 10$^2$ | 4.7 × 10$^4$ | 1.2 × 10$^6$ | 1.2 × 10$^6$ |
| Staphylococcus aureus | 8.2 × 10$^2$ | 2.9 × 10$^2$ | 3.2 × 10$^2$ | 1.6 × 10$^4$ | 3.5 × 10$^6$ | 3.5 × 10$^6$ |
| Escherichia coli | 1.3 × 10$^4$ | 6.8 × 10$^3$ | 8.5 × 10$^3$ | 1.2 × 10$^3$ | 2.2 × 10$^6$ | 2.2 × 10$^6$ |
| Bacillus subtilis | 7.6 × 10$^2$ | 6.1 × 10$^2$ | 9.5 × 10$^2$ | 6.3 × 10$^4$ | 3.0 × 10$^6$ | 3.0 × 10$^6$ |
| Salmonella enteritidis | 7.5 × 10$^4$ | 4.5 × 10$^4$ | 5.6 × 10$^4$ | 1.4 × 10$^4$ | 4.5 × 10$^6$ | 4.5 × 10$^6$ |

Test Example 4: Test of Persistency of Bactericidal Power on Eggshell

Each of bactericide shown in Table 8 was sprayed on a sterilized eggshell of hen (15 μl/cm$^2$), and allowed to stand for seven days in a sterilized room to be dried. Each of the bacteria suspension previously cultured in a similar manner to that described above was diluted with physiological saline. Then, 10 μl of the diluted suspension was spread on the eggshell. After allowed to stand for 10 minutes, bacterium on the egg shell were wiped with absorbent cotton, and liberated into physiological saline. Then, visible count was counted. Water was used as a blank, and 70% ethanol as a conventional bactericide was used as a control. The results of Examples were shown in Table 14, and the results of Comparative Examples were shown in Table 15. The bactericidal power of each of the bactericide containing both eucalyptus extract and chitosan (Examples 1 to 3) was stronger than that of a bactericide containing only chitosan (Comparative Example 4) or bactericides containing only eucalyptus extract (Comparative Examples 1 to 3). Namely, bactericidal power of each bactericide of Examples was maintained, even after elapse of seven days, on the surface of the eggshell.

TABLE 14

Persistency of bactericidal power of bactericides

| | Viable count (After 7 days) (Number/100 cm$^2$) | | |
|---|---|---|---|
| Strain | Example 1 | Example 2 | Example 3 |
| Staphylococcus aureus | 10 | <10 | 10 |
| Escherichia coli | 80 | 40 | 60 |
| Bacillus subtilis | <10 | <10 | 10 |
| Salmonella enteritidis | 80 | 50 | 80 |

TABLE 15

Persistency of bactericidal power of bactericides

| | Viable count (After 7 days) (Number/100 cm$^2$) | | | | | |
|---|---|---|---|---|---|---|
| | Comparative Example 1 | Comparative Example 2 | Comparative Example 3 | Comparative Example 4 | 70% Ethanol | No Treatment |
| Staphylococcus aureus | 1.2 × 10$^3$ | 6.7 × 10$^2$ | 8.5 × 10$^2$ | 2.3 × 10$^4$ | 2.4 × 10$^6$ | 2.4 × 10$^6$ |
| Escherichia coli | 1.4 × 10$^4$ | 8.6 × 10$^3$ | 1.1 × 10$^4$ | 2.5 × 10$^3$ | 1.5 × 10$^6$ | 1.6 × 10$^6$ |
| Bacillus subtilis | 7.8 × 10$^2$ | 6.3 × 10$^2$ | 9.6 × 10$^2$ | 8.5 × 10$^4$ | 3.2 × 10$^6$ | 3.2 × 10$^6$ |
| Salmonella enteritidis | 5.7 × 10$^4$ | 3.1 × 10$^4$ | 4.6 × 10$^4$ | 1.6 × 10$^4$ | 1.8 × 10$^6$ | 1.8 × 10$^6$ |

Example 4

Eucalyptus extract obtained in Example 2, chitosan, glycerol fatty acid ester and other components were mixed at a mixing ratio shown in Table 16, to prepare bactericides of Example 4 and Comparative Example 5. Amounts of eucalyptus extract and chitosan were shown in % by weight, and amounts of lactic acid and ethanol were shown in % by volume.

TABLE 16

Composition of bactericide

| | Example 4 | Comparative Example 5 |
|---|---|---|
| Eucalyptus extract | E. globulus 0.010% | E. globulus 0.010% |
| Chitosan | 0.010% | 0.010% |
| Lactic acid | 0.010% | 0.010% |
| Ethanol | 1% | 1% |
| Glycerol fatty acid ester | 0.05% | No addition |

Test Example 5: Test of Persistency of Bactericidal Power on Stainless Steel (effect of glycerol fatty acid ester)

Persistency of bactericidal power of the bactericides shown in Table 16 was evaluated in a similar manner to that of Test Example 3 (allowed to stand for one month). Results are shown in Table 17. After elapse of one month from spraying of the bactericide, bactericidal power of the bactericide containing glycerol fatty acid ester in addition to eucalyptus extract and chitosan (Example 4) was stronger than that of bactericides containing no glycerol fatty acid ester (Comparative Example 5).

TABLE 17

Persistency of bactericidal power of bactericides

| | Viable count (After one month) (Number/100 cm$^2$) | | |
|---|---|---|---|
| | Example 4 | Comparative Example 5 | No treatment |
| MRSA | 70 | 5.6 × 10$^3$ | 1.7 × 10$^5$ |
| Staphylococcus aureus | 80 | 4.5 × 10$^3$ | 2.4 × 10$^5$ |
| Escherichia coli | 1.4 × 10$^2$ | 2.0 × 10$^4$ | 3.5 × 10$^5$ |
| Bacillus subtilis | 60 | 6.2 × 10$^3$ | 1.5 × 10$^5$ |
| Salmonella enteritidis | 1.5 × 10$^2$ | 2.5 × 10$^4$ | 2.0 × 10$^5$ |

Examples 5 to 7

Eucalyptus extract obtained in Preparation Example 5, chitosan, and other components were mixed at a mixing ratio shown in Table 18, to prepare bactericides of Examples 5 to 7. Amount of chitosan was shown in % by weight, and amounts of eucalyptus extract and lactic acid were shown in % by volume.

TABLE 18

Composition of bactericides

| | Example 5 | Example 6 | Example 7 |
|---|---|---|---|
| Eucalyptus extract | E. viminalis 1.0% | E. globulus 1.0% | E. maculata 1.0% |
| Chitosan | 0.010% | 0.010% | 0.010% |
| Lactic acid | 0.010% | 0.010% | 0.010% |

Test Example 6: Persistency Test of Bactericidal Power on Paper

Persistency of bactericidal power of the bactericides shown in Table 18 was evaluated in a similar manner to that of Test Example 1 (allowed to stand for 7 days). Results are shown in Table 19. Even after elapse of 7 days from coating of the bactericide, bactericidal power of each of the bactericides of examples containing both eucalyptus extract and chitosan was strong.

TABLE 19

Persistency of bactericidal power of bactericides

| | Viable count (After 7 days) (Number/Disk) | | | |
|---|---|---|---|---|
| | Example 1 | Example 2 | Example 3 | Water |
| MRSA | <10 | <10 | <10 | 2.5 × 10$^5$ |
| Staphylococcus aureus | <10 | <10 | <10 | 2.4 × 10$^5$ |
| Escherichia coli | 30 | 50 | 60 | 3.5 × 10$^5$ |
| Salmonella typhimurium | 2.0 × 10$^2$ | 1.2 × 10$^2$ | 1.8 × 10$^2$ | 5.4 × 10$^5$ |
| Salmonella enteritidis | 60 | 60 | 80 | 1.2 × 10$^5$ |
| Pseudomonas putida | 10 | 20 | 40 | 3.2 × 10$^5$ |
| Bacillus subtilis | <10 | <10 | <10 | 6.3 × 10$^5$ |
| Bacillus cereus | <10 | <10 | <10 | 5.0 × 10$^5$ |
| Vibrio parahaemolyticus | <10 | <10 | <10 | 3.4 × 10$^5$ |
| Arthrobacter globiformis | <10 | <10 | <10 | 2.0 × 10$^5$ |
| Brevibacterium linens | <10 | <10 | <10 | 4.8 × 10$^5$ |
| Proteus vulgaris | 90 | 70 | 1.2 × 10$^2$ | 7.2 × 10$^5$ |
| Propionibacterium acnes | <10 | <10 | <10 | 2.3 × 10$^5$ |

Examples 8 and 9

Eucalyptus extract prepared in Preparation Example 3 (E. globulus, E. maculata) and chitosan, and other components were mixed at a mixing ratio shown in Table 20, to provide bactericides of Examples 8 and 9 and Comparative Examples 6 to 9. Amounts of eucalyptus extract and chitosan were shown in % by weight, and amounts of lactic acid and ethanol were shown in % by volume.

TABLE 20

Composition of bactericides

| | Example 8 | Example 9 | Comparative Example 6 | Comparative Example 7 | Comparative Example 8 | Comparative Example 9 |
|---|---|---|---|---|---|---|
| Eucalyptus extract | E. glo 0.020% | E. mac 0.020% | E. glo 0.040% | E. mac 0.040% | No addition | No addition |
| Chitosan | 0.020% | 0.020% | No addition | No addition | 0.040% | No addition |
| Lactic acid | 0.020% | 0.020% | 0.020% | 0.020% | 0.020% | 0.020% |
| Ethanol | 5% | 5% | 5% | 5% | 5% | 5% |

E. glo: E. globulus,
E. mac: E. maculata

[Test Example 7] Test of Bactericidal Power of Bactericides in the Case of Being Mixed With Meat Extract It was evaluated whether bactericidal power was lowered when the bactericides shown in Table 20 were mixed with beef extract (Wako Junyaku) according to the following method. For comparison, sodium hypochlorite was also evaluated. Strains used herein were Staphylococcus aureus IFO12732 and Salmonella enteritidis IFO03313.

One ml of each of bactericides shown in Table 20 and one ml of 5% beef extract (dissolved in sterilized water) were mixed at a ratio of one to one, and allowed to stand at a room temperature. After 10 minutes, 10 μl of bacteria suspension previously prepared was added to each of the bactericides and the mixture, and allowed to stand after stirred. Change of number of bacteria in the mixture solution was determined (one minute, five minutes and 10 minutes after addition of bacteria). According to previous experiments, it was confirmed that general viable count was 10 or less per one ml of 5% beef extract. As shown in Table 21 and Table 22, when 0.02% of sodium hypochlorite was mixed with a beef extract, bactericidal power thereof was lowered.

On the contrary, when the bactericides containing eucalyptus extract and chitosan (Examples 8 and 9) were mixed with beef extract, bactericidal power thereof was not lowered. The bactericidal power of each of the bactericide containing both eucalyptus extract and chitosan (Examples 8 and 9) was stronger than that of bactericides containing only eucalyptus extract (Comparative Examples 6 and 7) or a bactericide containing only chitosan (Comparative Example 8).

TABLE 21

Bactericidal power of bactericides after treating beef extract

| Mixing treatment of beef extract and bactericide (10 min) | | Staphylococcus aureus Viable count(Number/ml) | |
|---|---|---|---|
| | 1 min | 5 min | 10 min |
| Example 8 | done | $8.6 \times 10^4$ | <200 | <200 |
| Example 8 | none | $6.3 \times 10^4$ | <200 | <200 |
| Example 9 | done | $4.3 \times 10^4$ | <200 | <200 |
| Example 9 | none | $3.5 \times 10^4$ | <200 | <200 |
| Comparative Example 6 | done | $2.1 \times 10^5$ | $2.5 \times 10^3$ | <200 |
| Comparative Example 7 | done | $1.8 \times 10^5$ | $1.4 \times 10^3$ | <200 |
| Comparative Example 8 | done | $2.8 \times 10^5$ | $7.8 \times 10^4$ | $9.6 \times 10^3$ |
| Comparative Example 9 | done | $6.7 \times 10^6$ | $6.5 \times 10^6$ | $6.5 \times 10^6$ |
| 0.02% Sodium hypochloryte | done | $6.5 \times 10^6$ | $6.5 \times 10^6$ | $6.4 \times 10^6$ |
| 0.02% Sodium hypochloryte | none | <200 | <200 | <200 |

Number of inoculated bacteria: $6.7 \times 10^6$/ml

TABLE 22

Bactericidal power of bactericides after treating beef extract

| Mixing treatment of beef extract and bactericide (10 min) | | Salmonella enteritidis Viable count(Number/ml) | |
|---|---|---|---|
| | 1 min | 5 min | 10 min |
| Example 8 | done | $4.1 \times 10^4$ | $2.1 \times 10^4$ | <200 |
| Example 8 | none | $2.6 \times 10^4$ | $1.0 \times 10^4$ | <200 |
| Example 9 | done | $2.2 \times 10^4$ | $8.0 \times 10^3$ | <200 |
| Example 9 | none | $1.6 \times 10^4$ | $5.3 \times 10^3$ | <200 |
| Comparative Example 6 | done | $4.3 \times 10^5$ | $2.1 \times 10^5$ | $8.2 \times 10^4$ |
| Comparative Example 7 | done | $2.3 \times 10^5$ | $1.2 \times 10^5$ | $6.5 \times 10^4$ |
| Comparative Example 8 | done | $9.5 \times 10^4$ | $6.6 \times 10^4$ | $2.2 \times 10^3$ |
| Comparative Example 9 | done | $4.5 \times 10^5$ | $4.5 \times 10^5$ | $4.5 \times 10^5$ |
| 0.02% Sodium hypochloryte | done | $4.5 \times 10^5$ | $4.3 \times 10^5$ | $4.3 \times 10^5$ |
| 0.02% Sodium hypochloryte | none | <200 | <200 | <200 |

Number of inoculated bacteria: $4.6 \times 10^6$/ml

Examples 10 and 11

Eucalyptus extract prepared in Preparation Example 5 (*E. globulus, E. maculata*) and chitosan, and lactic acid were mixed at a mixing ratio shown in Table 23, to provide bactericides of Examples 10 and 11. Amounts of eucalyptus extract and lactic acid were shown in % by volume, and amount of chitosan was shown in % by weight.

TABLE 23

Composition of bactericides

| | Example 10 | Example 11 |
|---|---|---|
| Eucalyptus extract | *E.globulus* 1.0% | *E.maculata* 1.0% |
| Chitosan | 0.020% | 0.020% |
| Lactic acid | 0.020% | 0.020% |

Test Example 8: Test of Bactericidal Power of Bactericides in the Case of Being Mixed with Meat Extract The bactericides shown in Table 23 were examined for bactericidal power in a similar manner to that of Test Example 7. Results are shown in Table 24. Each of the bactericides of Examples had a strong bactericidal power.

TABLE 24

Bactericidal power of bactericides after treating beef extract

| Mixing treatment of beef extract and bactericide (10 min) | | Staphylococcus aureus Viable count (Number/ml) | |
|---|---|---|---|
| | 1 min | 5 min | 10 min |
| Example 10 | done | $1.2 \times 10^5$ | <200 | <200 |
| Example 10 | none | $1.0 \times 10^5$ | <200 | <200 |
| Example 11 | done | $8.4 \times 10^4$ | <200 | <200 |
| Example 11 | none | $5.6 \times 10^4$ | <200 | <200 |

Number of inoculated bacteria: $7.5 \times 10^6$/mL

Examples 12 and 13

Eucalyptus extract prepared in Preparation Example 5 (*E. globulus*) and chitosan, and lactic acid were mixed at a mixing ratio shown in Table 25, to provide bactericides of Examples 12 and 13 and Comparative Examples 10 and 11. Amounts of eucalyptus extract (propylene glycol extract) and lactic acid were shown in % by volume, and amount of chitosan was shown in % by weight.

TABLE 25

Composition of bactericides

| | Example 12 | Example 13 | Comparative Example 10 | Comparative Example 11 |
|---|---|---|---|---|
| Eucalyptus extract | *E. globulus* 1.0% | *E. globulus* 1.0% | No addition | No addition |
| Chitosan | 0.030% | 0.030% | No addition | No addition |
| Lactic acid | 0.030% | 0.30% | 0.030% | 0.30% |

Test Example 9: Test of Bactericidal Power of Bactericides in the Case of Being Mixed with Meat 100 ml of each of bactericides shown in Table 25 was charged into a vessel. 21 g of beef (block) was immersed in the bactericide, and allowed to stand at room temperature. After 24 hours, the beef was removed, and general bacterium (bacterium liberated from the beef) present in the bactericide were removed using a sterilized filter. 30 μl of bacteria suspension of *Staphylococcus aureus* or *Salmonella enteritidis* was added to 2 ml of the bactericide after used for the treatment of the beef. After five minutes, the number of bacterium in the bactericide was counted. As for 0.01% sodium hypochlorite, a similar test was conducted, and the results were compared.

As shown in Table 26, when 0.01% of sodium hypochlorite was mixed with a beef extract, bactericidal power thereof against *Staphylococcus aureus* or *Salmonella enteritidis* was lowered. When the bactericide containing eucalyptus extract and chitosan wherein concentration of lactic acid is 0.030% (Example 12) was mixed with a beef, bactericidal power thereof against *Staphylococcus aureus* was not lowered, but bactericidal power against *Salmonella enteritidis* was lowered.

In that case, pH of the bactericide increased from 4.2 (before sterilization) to 5.9 (after sterilization).

In the case of the bactericidal power of the bactericide wherein concentration of lactic acid is 0.30% (Example 13), the strong bactericidal power thereof against *Staphylococcus aureus* and *Salmonella enteritidis* was not lowered. In that case, pH of the bactericide increased from 3.1 (before sterilization) to 4.8 (after sterilization).

As shown in the above-mentioned results, pH of the bactericide increased due to the components from the beef during the sterilization of the beef, resulting in lowering of bactericidal power. However, it has been found that such lowering of bactericidal power can be prevented by adding lactic acid to the bactericide in high concentration so that pH of the bactericide can be maintained low (to about pH 4.8).

TABLE 27

Number of bacterium on the surface of beef treated with bactericides

| | Number of general bacterium (Number/g) | | |
|---|---|---|---|
| | After one day | After 3 days | After 6 days |
| Sterilized water | $2.0 \times 10^3$ | $1.6 \times 10^5$ | $4.3 \times 10^7$ |
| 0.01% Sodium hypochlorite | $6.7 \times 10^2$ | $1.4 \times 10^5$ | $3.4 \times 10^7$ |
| Example 12 | <200 | <200 | $2.4 \times 10^3$ |
| Comparative Example 10 | <200 | <200 | $3.6 \times 10^3$ |

Number of general bacteria on the surface of the beef before treatment with bactericide: <10/g Example 14

The fodder having a composition shown in Table 28 was prepared, and subjected to dry heat sterilization. Each component was shown in % by weight. Eucalyptus extract prepared in Preparation Example 2 (*E. globulus*) and chitosan, and other components were mixed at a mixing ratio shown in Table 29, to provide bactericides of Example 14

TABLE 26

Bactericidal power of bactericides after treating beef

| Bactericide | Treatment of beef | pH of bactericide before treatment of beef | pH of bactericide after treatment of beef | *Salmonella enteritidis* Viable count (Number/ml) | | *Staphylococcus aureus* Viable count (Number/ml) | |
|---|---|---|---|---|---|---|---|
| | | | | 0 min | 5 min | 0 min | 5 min |
| 0.01% Sodium hypochlorite | done | — | — | $2.1 \times 10^5$ | $1.5 \times 10^5$ | $5.0 \times 10^5$ | $1.8 \times 10^5$ |
| 0.01% Sodium hypochlorite | none | — | — | $2.1 \times 10^5$ | <1000 | $5.0 \times 10^5$ | <1000 |
| Example 12 | done | 4.2 | 5.9 | $2.1 \times 10^5$ | $1.0 \times 10^5$ | $5.0 \times 10^5$ | 1000 |
| Example 12 | none | — | — | $2.1 \times 10^5$ | <1000 | $5.0 \times 10^5$ | <1000 |
| Example 13 | done | 3.1 | 4.7 | $2.1 \times 10^5$ | <1000 | $5.0 \times 10^5$ | <1000 |
| Example 13 | none | — | — | $2.1 \times 10^5$ | <1000 | $5.0 \times 10^5$ | <1000 |
| Comparative Example 10 | done | 4.2 | 5.9 | $2.1 \times 10^5$ | $4.6 \times 10^5$ | $5.0 \times 10^5$ | $5.0 \times 10^5$ |
| Comparative Example 11 | done | 3.1 | 4.7 | $2.1 \times 10^5$ | $4.0 \times 10^5$ | $5.0 \times 10^5$ | $4.7 \times 10^5$ |

Test Example 10: Measurement of Number of Bacterium on the Surface of Beef Treated with Bactericide The bactericides of Example 12 and Comparative Example 10 shown in Table 25 were used in the following experiments.

50 ml of each of bactericides was charged in a vessel, and then 15 g of beef (block) was immersed in the bactericide, and allowed to stand at room temperature (surface sterilization). After 5 minutes, the bactericide was removed, and only the beef was preserved in the vessel at 4° C. After certain period (① after one day, ② after three days, ③ after six days), 25 ml of physiological saline was added to the vessel containing the beef, and shaked. The number of the bacterium cells liberated from the beef into the physiological saline was counted. It was confirmed according to preliminary experiments that the number of the bacterium cells per one gram of the beef existing on the surface of the beef before sterilization treatment was 10 or less. Sterilized water and sodium hypochlorite were also examined.

The number of the bacterium cells (per one gram of the beef) existing on the surface of the beef after the treatment with each of the bactericides was shown in Table 27. When the beef was treated with the bactericide containing both of the eucalyptus extract and chitosan (Example 9), propagation of bacterium on the surface of the beef was strongly inhibited compared with the beef treated with sterilized water and the beef treated with 0.01% of sodium hypochlorite.

and Comparative Examples 11 and 12. Amounts of eucalyptus extract and chitosan were shown in % by weight, and amounts of lactic acid, ethanol and sterilized water were shown in % by volume.

TABLE 28

Composition of fodder

| Raw material | ratio (%) |
|---|---|
| Soy bean protein powder | 45 |
| Wheat powder | 27 |
| Powdered oil | 15 |
| Corn starch powder | 10 |
| Premix | 3 |

TABLE 29

Composition of bactericides

| | Example 14 | Comparative Example 11 | Comparative Example 12 |
|---|---|---|---|
| Ethanol extract of eucalyptus | 0.02% | No addition | No addition |
| Chitosan | 0.03% | No addition | No addition |
| Lactic acid | 0.03% | 0.03% | No addition |
| Ethanol | 10% | 10% | No addition |
| Sterilized water | 100% | 100% | 100% |

Test Example 11: Test of Bactericidal Power of Fodder Containing Bactericide 10 ml of each of the bactericides of Example 14 and Comparative Examples 11 and 12 shown in Table 29 was mixed with 10 g of the fodder shown in Table 28, and dried. One g of the fodder was impregnated with 50 µl of the bacterium solution prepared by diluting a bacterium solution of *Escherichia coli* IFO12734 previously cultured under the condition shown in Table 1 with physiological saline, and allowed to stand at room temperature. After certain period (after three days, after six days, after 15 days), physiological saline was added to the fodder, stirred to liberate bacterium existing in the fodder. The viable count in the physiological saline was determined, and the viable count per one g of the fodder was calculated. The results were shown in Table 30. When the fodder containing both of the eucalyptus extract and chitosan (Example 14), propagation of bacterium in the fodder was inhibited compared with control (Comparative Examples 11 and 12).

TABLE 30

Bactericidal power of fodder

|  | Number of inoculated bacteria (Number/g) | Viable count (Number/g) *Escherichia coli* | | |
| --- | --- | --- | --- | --- |
|  |  | After 3 days | After 6 days | After 15 days |
| Example 14 | 2.2 × 10$^4$ | <200 | <200 | 1.2 × 10$^3$ |
| Comparative Example 11 | 2.2 × 10$^4$ | 8.4 × 10$^4$ | 1.4 × 10$^6$ | 2.1 × 10$^8$ |
| Comparative Example 12 | 2.2 × 10$^4$ | 8.6 × 10$^4$ | 1.4 × 10$^6$ | 1.2 × 10$^8$ |

Example 15

Eucalyptus extract prepared in Preparation Example 2 and chitosan, and other components were mixed at a mixing ratio shown in Table 31, to provide bactericides of Example 15 and Comparative Example 13. Amounts of the eucalyptus extract and chitosan were shown in % by weight, and an amount of lactic acid was shown in % by volume.

TABLE 31

Composition of bactericides

|  | Example 15 | Comparative Example 13 |
| --- | --- | --- |
| Eucalyptus extract | *E. globulus* 0.010% | No addition |
| Chitosan | 0.010% | No addition |
| Lactic acid | 0.010% | 0.010% |
| Ethanol | 5% | 5% |

[Test Example 12] Persistency Test of Bactericidal Power of Wet Tissue 20 g of tissue paper was impregnated with 100 ml of each of bactericides shown in Table 31 to prepare wet tissue. A corner (1 cm×1 cm) of a stainless steel plate previously sterilized in a sterilized room was wiped with the wet tissue and allowed to stand for 24 hours. 10 µl of bacterium suspension of each strain was placed on the stainless steel plate. After allowed to stand for 10 minutes, the stainless steel plate was wiped with a sterilized cotton swab on a stick, which was then put in physiological saline and stirred. A certain amount of the physiological saline was spread on agar medium to determine viable count.

The results were shown in Table 32. When the stainless steel was wiped with the wet tissue impregnated with the bactericide of Example 15, strong bactericidal power was maintained on the stainless steel even after 24 hours.

TABLE 32

Persistency of bactericidal power on stainless steel wiped with wet tissue

|  | Number of inoculated bacteria (Number/ml) | Viable count (Number/100 cm$^2$) | |
| --- | --- | --- | --- |
|  |  | Example 15 | Comparative Example 13 |
| *Staphylococcus aureus* | 1.2 × 10$^6$ | <100 | 1.1 × 10$^6$ |
| MRSA | 2.5 × 10$^6$ | <100 | 2.5 × 10$^6$ |
| *Escherichia coli* | 8.4 × 10$^5$ | <100 | 8.5 × 10$^5$ |
| *Bacillus subtilis* | 6.5 × 10$^5$ | <100 | 6.5 × 10$^5$ |

Example 16

Eucalyptus extract prepared in Preparation Example 2 and chitosan, and other components were mixed at a mixing ratio shown in Table 33, to provide bactericides of Examples 16 and Comparative Example 14. Amounts of eucalyptus extract and chitosan were shown in % by weight, and an amount of lactic acid was shown in % by volume.

TABLE 33

Composition of bactericides

|  | Example 16 | Comparative Example 14 |
| --- | --- | --- |
| Ethanol extract of eucalyptus | *E. globlus* 0.010% | No addition |
| Chitosan | 0.020% | No addition |
| Lactic acid | 0.020% | 0.020% |
| Ethanol | 50% | 50% |

Test Example 13: Test of Bactericidal Power on Diaper 15 g of diaper paper (30×65 cm) was impregnated with 100 ml of each bactericides shown in Table 33 to prepare a paper diaper. The paper diaper was cut into regular square (1 cm×1 cm), and then sterilized in autoclave. 0.75 of a cut piece of the diaper was put in a 300 ml Erlenmeyer flask (containing 70 ml of physiological saline). 5 ml of a bacteria suspension of each strain was added to the Erlenmeyer flask, and shaked at 25° C. (320 rpm: round per minute). After one hour, one ml of the physiological saline was taken, diluted, and then spread on agar medium. Thereby, a viable count in the physiological saline was determined. The sterilization rate was determined also in the case that a diaper was not impregnated with bactericide. The sterilization rate was calculated by the following formula: Sterilization Rate= (number of inculated bacterium cells−number of bacterium cells after shaking)/number of inoculated bacterium cells× 100. The results were shown in Table 3. The sterilization rate of the diaper impregnated with the bactericide containing the eucalyptus extract and chitosan (Example 16) was 99.9% as for each bacteria. Accordingly, it was found that the diaper had a strong bactericidal power compared with control.

TABLE 34

Sterilization rate

| | Number of inoculated bacteria (Number/ml) | Sterilization rate (%) | |
|---|---|---|---|
| | | Example 16 | Comparative Example 14 |
| MRSA | $2.4 \times 10^4$ | 99.9 | 0 |
| Proteus vulgaris | $1.5 \times 10^4$ | 99.9 | 0 |

Example 17

The eucalyptus extract prepared in Preparation Example 2, chitosan, glycerol fatty acid ester, and other components were mixed at a mixing ratio shown in Table 35, to provide bactericides of Example 17 and Comparative Example 15. Amounts of eucalyptus extract and chitosan were shown in % by weight, and amounts of glycerol fatty acid ester and lactic acid were shown in % by volume.

TABLE 35

Composition of Bactericides

| | Example 17 | Comparative Example 15 | Comparative Example 16 | Comparative Example 17 |
|---|---|---|---|---|
| Eucalyptus extract | E. globulus 0.010% | E. globulus 0.010% | No addition | No addition |
| Chitosan | 0.010% | 0.010% | 0.010% | 0.010% |
| Lactic acid | 0.010% | 0.010% | 0.010% | 0.010% |
| Ethanol | 1% | 1% | 1% | 1% |
| Glycerol fatty acid ester | 0.05% | No addition | 0.05% | No addition |

Test Example 14: Fungicidal Power Test

50 μl of a spore suspension of fungus (*Aspergillus niger* IF09455, *Penicillium citrinum* IF06352) was added to a sterilized test tube containing one ml of the fungicide shown in Table 35, stirred and then allowed to stand at room temperature. After one hour, a certain amount thereof was spread on potato dextrose medium to determine the number of fungus colony (viable count). The results were shown in Table 36. It was found that the fungicidal power against fungi (*Aspergillus niger*, *Penicillium citrinum*) of the fungicide containing both eucalyptus extract and chitosan (Example 17) was stronger than that of the fungicide containing only eucalyptus extract (Comparative Example 15) or the fungicide containing only glycerol fatty acid ester (Comparative Example 16).

TABLE 36

Fungicidal power of fungicide

| | Number of inoculated bacteria (Number/ml) | Number of colony (Number/ml) | | | |
|---|---|---|---|---|---|
| | | Example 17 | Comparative Example 15 | Comparative Example 16 | Comparative Example 17 |
| Aspergillus niger | $2.0 \times 10^4$ | <10 | $6.2 \times 10^3$ | $4.3 \times 10^3$ | $2.0 \times 10^4$ |
| Penicillium citrinum | $1.5 \times 10^4$ | <10 | $4.5 \times 10^3$ | $3.7 \times 10^3$ | $1.5 \times 10^4$ |

Test Example 15: Fungicidal Power Test 15 g of diaper paper (30 cm×65 cm) was impregnated with 100 ml of fungicide of Example 17 shown in Table 35 and dried, to prepare a paper diaper. The paper diaper was cut into regular square (1 cm×1 cm), and then sterilized in autoclave. It was then put on potato dextrin medium inoculated with a spore suspension of fungus (*Aspergillus niger*, *Penicillium citrinum*), and allowed to stand and cultured at 28° C for 7 days. A diaper that was not impregnated with the fungicide was used as a control. The results were shown in Table 37. When the fungicide of Example 17 was used, block circle (zone of inhibition) was formed, which shows an effective antifungal power.

TABLE 37

Fungicidal power of diaper

| | Formation of blocking circle (halo) | |
|---|---|---|
| | Example 17 | No addition |
| Aspergillus niger | + | − |
| Penicillium citrinum | + | − |

+: Formative, −: No formation

Test Example 16: Acute Toxity Test

The eucalyptus extract prepared in Preparation Example 2 was dissolved in ethanol/olive oil (1/1), and dosed orally or by hypodermic injection to 45-day old mouse. Ten mouse were used per each test standard. Acute toxicity test was conducted with six standards of from 0.5 to 14.5 g/kg as for oral administration and with six standards of from 0.3 to 6.5 g/kg as for hypodermic injection. The mouse were observed for two weeks. The mouse lived in all test standards, without no abnormality in skin. The results of toxicity test were far higher than $LD_{50}$ in mouse hypodermic injection >0.2 g/kg that is acute toxicity criteria for regular pharmaceuticals provided by the Ministry of Health and Welfare. Accordingly, it was shown that the bactericide was highly safe pharmaceutical or quasi drug.

Industrial Availability

As described above, the bactericide (and the fungicide) of the present invention can be used as:

1. a bactericide (and a fungicide) for household articles such as tables, tablewares, chopping boards, cooking stands, toilet seats at home or restaurants; cattle sheds, chicken houses, instruments in buildings for keeping animals; machines at abattoir facilities; skin of human or animals, egg shells of hens, quails or the like;

2. a bactericide (and a fungicide) for doors, knobs of doors, floors, handrail of beds, medical equipments such as instruments for operation, medical facilities at hospitals or old-age homes; fresh foods such as meat, fishes, vegetables; seeds of plants;

3. a bactericide (and a fungicide) for affording a bactericidal power to: living things such as wet tissues, diapers, sheets, clothes, sanitary cotton, wipers for hip, non-woven textiles, oil removing papers, papers (sheets) for food packing, papers (sheets) for laying under the foods, the paper mule, moist hand towels, towels, coverings, or the like; fodder for animals, fishes or the like; foods, for example, gum, candies, products made of boiled fish pastes such as semicylindrical boiled fish paste (kamaboko), tubular rolls of boiled fish paste (chikuwa) or the like, livestock products such as sausages, hams or the like, confectioneries, japanese confectioneries, noodles such as undried noodles, buckwheat noodles (soba) or the like, seasonings such as sauce, soy sauce, or the likes, pickles, delicatessen, processed foods of eggs, sandwiches, mayonnaise, cream puff or the like;

4. a bactericide (and a fungicide) for being mixed in cosmetics such as soaps, cleaning agents or cream or added to pharmaceuticals to be orally administrated.

What is claimed is:

1. A composition bactericide and/or fungicide comprising a polar organic solvent extract of leaves of eucalyptus plant, chitosan, and glycerol fatty acid ester.

2. A composition bactericide and/or fungicide comprising a polar organic solvent extract of leaves of eucalyptus plant and chitosan, the polar solvent selected from at least one of lower alcohols and glycols.

3. The composition of claim 1, wherein the polar solvent is selected from at least one of lower alcohols and glycols.

4. The composition of claim 1, wherein the extract comprises a eucalyptus fraction extracted into the polar organic solvent, wherein essential oil of the eucalyptus is previously removed by degreasing with a non-polar organic solvent or by steam distillation.

5. The composition of claim 4, wherein the solvent comprises one or more of halogenated hydrocarbons, ethers, fatty acid esters, ketones, and lower alcohols.

6. The composition of claim 4, wherein the non-polar organic solvent comprises one or more alkanes.

7. The composition of claim 2, wherein the extract comprises a eucalyptus fraction extracted into the polar organic solvent, wherein essential oil of the eucalyptus is previously removed by degreasing with a non-polar organic solvent or by steam distillation.

8. The composition of claim 7 wherein the solvent comprises one or more of halogenated hydrocarbons, ethers, fatty acid esters, ketones, and lower alcohols.

9. The composition of claim 7, wherein the non-polar organic solvent comprises one or more alkanes.

10. The composition of claim 1, wherein the extract and the chitosan together comprise about 0.0001 to 10% of the composition by weight, and the glycerol fatty acid ester comprises about 0.0001 to 20% of the composition by weight.

11. The composition of claim 2, wherein the extract and the chitosan together comprise about 0.0001 to 10% of the composition by weight, and further comprises glycerol fatty acid ester in an amount of about 0.0001 to 20% of the composition by weight.

12. An animal feed comprising a composition according to claim 1.

13. The composition of claim 1, wherein the composition is included in a wet tissue, towel, wipe, or diaper.

14. A method of treating propionibacterium acne comprising administering to a host in need of such treatment an effective amount of a composition according to claim 1.

15. A method of treating against trichophyton mentagrophytes comprising administering to a host in need of such treatment an effective amount of a composition according to claim 1.

16. A method of treating against aspergillus or pencitlium comprising administering an effective amount of a composition according to claim 1 to an infected area.

17. An eggshell sterilization method comprising adding an effective amount of a composition according to claim 1 to an eggshell.

18. A sterilization method comprising adding an effective amount of a composition according to claim 1 to living things, medical instruments, medical facilities or abattoir facilities.

19. A sterilization method comprising adding an effective amount of a composition according to claim 1 to fresh food.

20. The method of claim 19, wherein the food comprises meat or seeds of plants.

21. An animal feed comprising a composition according to claim 2.

22. The composition of claim 2, wherein the composition is included in a wet tissue, towel, wipe, or diaper.

23. A method of treating propionibacterium acne comprising administering to a host in need of such treatment an effective amount of a composition according to claim 2.

24. A method of treating against trichophyton mentagrophytes comprising administering to a host in need of such treatment an effective amount of a composition according to claim 2.

25. A method of treating against aspergillus or pencillium comprising administering an effective amount of a composition according to claim 2 to an infected area.

26. An eggshell sterilization method comprising adding an effective amount of a composition according to claim 2 to an eggshell.

27. A sterilization method comprising adding an effective amount of a composition according to claim 2 to living things, medical instruments, medical facilities or abattoir facilities.

28. A sterilization method comprising adding an effective amount of a composition according to claim 2 to fresh food.

29. The method of claim 28, wherein the food comprises meat or seeds of plants.

* * * * *

UNITED STATES PATENT AND TRADEMARK OFFICE
CERTIFICATE OF CORRECTION

PATENT NO.   : 6,352,727 B1
DATED        : March 5, 2002
INVENTOR(S)  : T. Takahashi It is certified that error appears in the above-identified patent and that said Letters Patent is hereby corrected as shown below:

Column 31,
Line 25, "A composition bactericide and/or fungicide" should be -- A bactericide and/or fungicide composition. --
Line 28, "A composition bactericide and/or fungicide" should be -- A bactericide and/or fungicide composition. --

Column 32,
Line 17, "pencitlium" should be -- pencillium --.

Signed and Sealed this

Fourth Day of February, 2003

JAMES E. ROGAN
*Director of the United States Patent and Trademark Office*